United States Patent [19]
Petersen et al.

[11] 4,227,974
[45] Oct. 14, 1980

[54] ELECTROCHEMICAL CELL HAVING A POLAROGRAPHIC DEVICE WITH ION SELECTIVE ELECTRODE AS WORKING ELECTRODE AND METHOD OF USE

[75] Inventors: Otto Petersen; Hans-Dieter Schmidt, both of Krefeld, Fed. Rep. of Germany

[73] Assignee: Bayer Aktiengesellschaft, Leverkusen, Fed. Rep. of Germany

[21] Appl. No.: 11,343

[22] Filed: Feb. 12, 1979

Related U.S. Application Data

[63] Continuation-in-part of Ser. No. 946,680, Sep. 28, 1978, abandoned, which is a continuation of Ser. No. 804,699, Jun. 8, 1977, abandoned.

[30] Foreign Application Priority Data

Jun. 18, 1976 [DE] Fed. Rep. of Germany ....... 2627271

[51] Int. Cl.$^2$ .............................................. G01N 27/46
[52] U.S. Cl. ................................ 204/1 T; 204/195 R; 204/195 P
[58] Field of Search ............... 204/195 R, 195 P, 1 N, 204/1 K, 1 F, 1 T; 324/29

[56] References Cited

U.S. PATENT DOCUMENTS

| 2,912,367 | 11/1959 | Asendorf et al. | 204/195 R X |
| 3,539,455 | 11/1970 | Clark | 204/195 P X |
| 3,776,832 | 12/1973 | Oswin et al. | 204/195 R X |
| 3,795,589 | 3/1974 | Dahms | 204/195 P X |
| 3,824,167 | 7/1974 | Oswin et al. | 204/195 R |
| 3,915,831 | 10/1975 | Riseman et al. | 204/195 P |
| 3,919,067 | 11/1975 | Carson et al. | 204/195 P |
| 3,950,231 | 4/1976 | Frandt et al. | 204/1 N |
| 4,001,103 | 1/1977 | Blurton et al. | 204/195 R |
| 4,013,522 | 3/1977 | Nischik et al. | 204/1 T |

FOREIGN PATENT DOCUMENTS

| 2013378 | 9/1971 | Fed. Rep. of Germany | 204/1 N |
| 2354149 | 6/1974 | Fed. Rep. of Germany | 204/195 |

OTHER PUBLICATIONS

Richard A. Durst, "Ion–Selective Electrodes," pp. 306–307, (1969).

Primary Examiner—G. L. Kaplan
Attorney, Agent, or Firm—Sprung, Felfe, Horn, Lynch & Kramer

[57] ABSTRACT

The sensitivity and, especially, the selectivity of a polarographic device can be increased by using an ion selective electrode as the working electrode in the electrochemical cell. The cell is a high sensitivity gas detector which is reliable in operation and which is particularly suitable for use in the field of environmental protection. Especially silver/silver iodide electrodes used in various electrolytes are particularly suitable for detecting hydrocyanic acid, phosgene and hydrogen sulphide.

10 Claims, 1 Drawing Figure

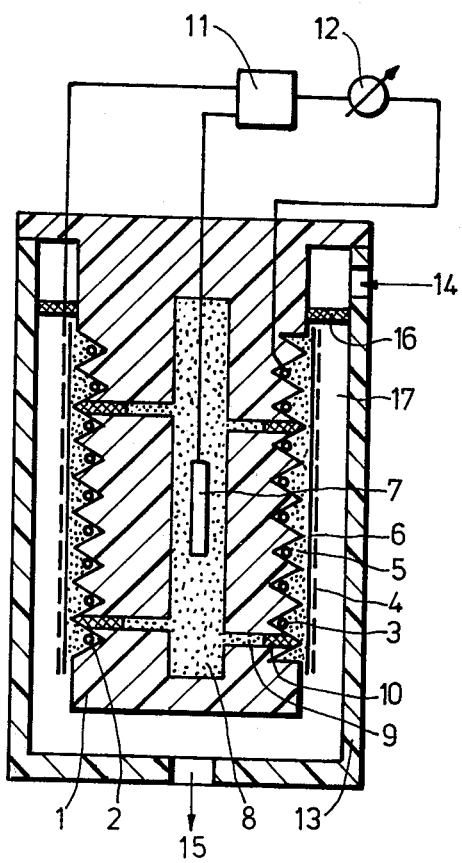

ELECTROCHEMICAL CELL HAVING A POLAROGRAPHIC DEVICE WITH ION SELECTIVE ELECTRODE AS WORKING ELECTRODE AND METHOD OF USE

This application is a continuation-in-part of application Ser. No. 946,680 filed Sept. 28, 1978 which is a continuation of application Ser. No. 804,699 filed June 8, 1977 and both now abandoned.

This invention relates to an electrochemical cell for the detection of a gas in a gas mixture. It contains a polarographic device and means for carrying the gas to the boundary between the working electrode and the electrolyte. The polarographic device consists of two electrodes, the working electrode and the auxiliary electrode, or of three electrodes, the working electrode, the auxiliary electrode and the reference electrode, and electrolyte and a potentiostat equipped with current measuring instrument. The voltage on the potentiostat for cathodic or anodic polarisation of the working electrode is adjusted to a value which is characterised for the component to be measured.

Electrochemical cells for detecting a gas in a gas mixture are particularly important in the field of environmental protection. They can be used for detecting the presence of dangerous gases in the atmosphere. In particular, they are intended to indicate when a given concentration is exceeded, and they must therefore be able to operate for prolonged periods with constant sensitivity and without requiring servicing.

In the measuring cells which have been developed so far, the selectivity and the selectivity are often insufficient. An electrochemical cell containing a polarographic device has been described in German Offenlegungsschrift No. 2,354,149. The polarisable working electrode (feeler electrode) is typically made of a noble metal. In this Offenlegungsschrift it is claimed as an inventive feature that a three-electrode arrangement is used instead of a two-electrode arrangement. The stability and sensitivity of the electrochemical cell are said to be thereby improved. However, this electrochemical cell is still insufficiently selective. The cell is sensitive to all components which have a polarographic level smaller than or equal to the set operating voltage.

The cell works according to the principle of conventional polarography. As is known, in this method of analysis the voltage at the working electrode is periodically increased from a minimum to a maximum polarisation. A diagram is obtained of the current of the electrochemical processes produced on the working electrode by this polarisation, as a function of the set voltage.

If a definite voltage is set in order to measure the current of a particular, desired process, all the undesired processes which occur up to this voltage also add up. A metal electrode is basically an electron conductor and thus allows all redox reactions of the following type:

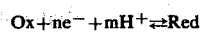

What is unsatisfactory in electrochemical cells of this type is the selectivity.

It is an object of the present invention to improve the sensitivity and particularly the selectivity of electrochemical cells containing a polarographic device for the measurement of the concentration of a gas in a gas mixture. The cell should be a high sensitivity gas detector, in particular for detecting minute quantities of dangerous gases in the air.

The electrochemical cell should also be reliable in operation, require little servicing and be easy to handle.

The problem is solved by using an ion selective electrode as a working electrode.

The essential part of the invention is to avoid the use of an electron-conductive electrode of type 1 (metal electrodes) and instead of this to use ion-conductive electrodes of type 2, which are, as is known, metals coated with a poorly soluble salt having the same cation. (e.g. silver coated with silver chloride). Ion selective electrodes are ion-conductive electrodes of type 2. Since the exchange of electric charges on the boundary surface of the working electrode/electrolytic measuring gas is thus no longer possible with electrons but can only be conducted by ions selected for the analysis, high selectivity thereby is achieved. Since the preparation of ions does not require such high polarisation voltage as the purely polarographic oxidation or reduction, by means of the considerable reduction of the required polarisation voltage a further contribution is made to the increase of the selectivity of a cell.

By means of an example the difference can be made clear between the reaction mechanisms when using electrodes of types 1 and 2: the example relates to the oxidation of hydrogen sulphide.

1. electrical oxidation of $H_2S$ at an electrode of type 1
   1.1 dissociation of $H_2S$ $$H_2S \rightleftharpoons 2H^+ + S^{2-}$$

1.2 anodic oxidation $$S^{2-} \rightarrow S^o + 2e^-$$

1.3 cathodic reduction:

$$2H_+ + 2e_- \rightarrow H_2^o$$

2. electrolytical oxidation of $H_2S$ at an electrode of type 2
   2.1 dissociation of $H_2S$:

$$H_2S \rightleftharpoons 2H^+ + S^{2-}$$

2.2 anodic oxidation on the $Ag_2S$-coated Ag-electrode:
   2.2.1 potential-changing process, caused by the $Ag_2S$-dissociation hindered by the $H_2S$-dissociation:

$$Ag_2S \rightleftharpoons 2Ag^+ + S^{2-}$$

2.2.2 electrochemical process which is initiated by the potential-retaining effect of a potentiostat:
   2.2.2.1 primary reaction $$2Ag^o \rightarrow 2Ag^+ + 2e^-$$

2.2.2.2 secondary reaction $$2Ag^+ + S^{2-} \rightarrow Ag_2S$$

2.3 cathodic reduction (on metal electrode):

$$2H^+ + 2e^- \rightarrow H_2$$

The example clearly shows that all electron transfers occur at an electrode of type 1 which are possible up to the set energy level, because the metal electrode can give off electrons directly and does not therefore select. An electrode of type 2 only changes its potential when the dissociation of its poorly soluble salt is disturbed by the addition of other ions. This disturbance is however only possible by means of a very limited number of ion-types. A potentiostat attempts to restore the disturbed equilibrium and can only do so by ionisation of the electrode material. The selection is achieved by this.

Ion selective electrodes have hitherto been used in combination with a reference electrode to form a galvanic cell which obeys Nernst's Law in delivering a voltage which is proportional to the logarithm of the concentration of ions to be measured in the electrolyte. An example of such a cell is a glass electrode/reference electrode dipped in an aqueous solution containing hydrogen ions for measuring the hydrogen ion concentration. A survey of ion-selective electrodes may be found in the book by K. Cammann entitled "Das Arbeiten mit ionenselektiven Elektroden", Springer-Verlag 1973.

In the apparatus according to the present invention, an ion-selective electrode is inserted as a working electrode in an electrochemical cell containing a polarographic device, i.e. the electrode is polarised by an external voltage source using a potentiostat. The selectivity of this electrode is thus maintained and a current, which is directly proportional to the ionic concentration to be measured, is produced. This ionic concentration may be obtained, for example, by dissolving and/or reacting the gas component to be measured in a suitable electrolyte.

The use of ion-selective electrodes in an electrochemical cell having a polarographic device provides the following improvements:

1. Electrochemical reaction of the unknown component on the working electrode converts this component into an electrochemically inactive substance or an insoluble substance. The measuring process is therefore, at the same time, a process of regeneration of the measuring device, in particular of the electrolyte, which now exercises only an indirect function. Continuous renewal of the electrolyte, which must be carried out when an ion-selective electrode is used in a galvanic cell, is now not necessary.

2. The quantity measured when an ion-selective electrode is used in a galvanic cell is the logarithm of a concentration, whereas in the arrangement according to the invention a linear characteristic is measured. The advantage obtained is a high degree of sensitivity which is constant over the whole range of measurement.

3. Owing to the logarithmic relationship between the concentration and voltage measured in a galvanic cell, such an arrangement has no definite zero point. In a polarographic arrangement with direct proportionality between current and concentration, on the other hand, a definite zero point is naturally given.

4. Provided the ion-selective electrode is suitably chosen with regard to the measurement problem to be carried out and the use of the electrode as working electrode in a polarographic device, and provided suitable polarisation is effected, the selectivity of the ion-selective electrode remains unchanged so that the transverse sensitivities of the measuring arrangement towards other components present in the gas are restricted or even completely eliminated. This is not the case, for example, with metallic working electrodes.

According to an advantageous development of this invention, the reference electrode is of the same type as the ion-selective working electrode. The result indicated by the instrument thus becomes virtually independent of temperature.

According to another advantageous embodiment of the electrochemical cell, the material of the auxiliary electrode is chosen so that when the gas under investigation contains the component which is to be measured, the action of the potentiostat caused the primary reaction product of the working electrode to become electrolytically inactive due to deposition on the auxiliary electrode.

According to further advantageous embodiments of the invention, the electrolyte situated between the working electrode and the auxiliary electrode is thickened and a porous diaphragm is arranged between the working electrode and the reference electrode. The electrolyte in the reference electrode chamber has the same chemical composition as the working electrolyte except that it contains no thickener.

Additional electrolyte can be supplied through the diaphragm channels when necessary to compensate for loss of working electrolyte by evaporation. The operational reliability of the apparatus is thereby considerably increased because servicing of the gas detector need only be carried out at very long intervals.

In another advantageous embodiment of the electrochemical cell, the working electrode is separated from the gas chamber by a membrane of polyethylene. Although the sensitivity of the gas detector is thereby slightly reduced, this can be compensated by subsequent increase in the amplification. The membrane is an effective barrier for water vapour and ensures that the electrolyte does not become diluted when water is present in the gas to be investigated.

An example of the electrochemical cell according to the invention for detecting a gas in a gas mixture is described below with reference to the accompanying drawing.

The auxiliary electrode 3 lies at the base of the screw thread 2 cut into the surface of a cylindrical body of polypropylene 1. A mesh wrapped round the threaded part of the cylinder 1 forms the working electrode 4. The electrolyte 5 between the auxiliary electrode 3 and the working electrode 4 is thickened. A foil 6 which is permeable to the electrolytes is advantageously arranged on the internal surface of the working electrode 4 to stabilise the electrolyte mechanically and to reduce the effective quantity of electrolyte, which is advantageous for the time factor. The reference electrode 7 is arranged centrally and dips into an electrolyte 8 which has the same composition as electrolyte 5 but without the thickener. The electrolyte 8 round the reference electrode 7 is electrically coupled to the thickened electrolyte 5 between the auxiliary electrode 3 through channels 9. A diaphragm 10 is installed in each channel 9. This prevents electrolyte 8 from flowing out but fresh electrolyte can be supplied through the diaphragm 10 so that the outer electrolyte 5, which is thickened, maintains its composition for a long time. The voltage of the polarographic stage of the gas which is to be detected is preselected on the potentiostat 11. The instrument 12 indicates a current proportional to the concentration. The polypropylene body 1 is surrounded by a polypropylene housing 13 having a gas inlet 14 and gas outlet 15. An annular frit 16 retains the gas to be measured and provides for a uniform flow of gas through the chamber 17.

EXAMPLES OF APPLICATION

1. Detection of hydrocyanic acid in air.

The working electrode 4 in the electrochemical cell is a cyanide-selective electrode, a silver net closely melted over with silver iodide. As reference electrode 7 a silver wire coated with silver chloride, preferably however with silver iodide, is used. The working electrode is polarised with −600 mV relating to a standard hydrogen electrode. The auxiliary electrode 3 is made of silver and is enclosed by $PbO_2$.

A mixture of 70% glycerine, 20% water, 5% sodium acetate and 5% methyl cellulose has proven to be appropriate for electrolyte 5. The mixture is dissolved when hot and is filled, in the form of a viscous liquid, into the space between the working and the auxiliary electrode. This composition gels by cooling. The space surrounding the reference electrode is filled with the same electrolyte, but without methyl cellulose. This electrolyte remains liquid because of this. In the presence of HCN the following processes take place in the electrode system:

1. Dissociation in the Ag/AgI electrode $$AgJ \rightleftarrows Ag^+ + I^-$$

2. This dissociation is disturbed by the complex binding of $Ag^+$ ions by HCl $$Ag^+ + J + 2HCN \rightarrow Ag(CN)_2^- + 2H^+ + I^-$$

3. The change in potential, produced by a shift in the dissociation equilibrium causes the potentiostat to react by a change in current, which causes the formation of $Ag^+$ ions from the electrode material $$2Ag^\circ \rightarrow 2Ag^+ + 2e^-$$

4. The Ag ions are used for the readjustment of the equilibrium $$2Ag^+ + Ag(CN)_2^- + I^- \rightarrow 2Ag\ Cn + AgI$$

$H^+$ ions are discharged at the metallic auxiliary electrode.

$$2H^+ + 2e^- \rightarrow H_2$$

It is not difficult to recognize from this reaction mechanism the advantage of the use of an ion-selective electrode. Since the electrode only reacts towards a few substances by a change in voltage (because AgI only reacts with a few other substances), a higher degree of Selectivity is achieved. By setting an optimum polarisation voltage of the working electrode from −600 mV relating to the standard hydrogen electrode the partial reactions 2 to 5 are preferred. Polarisation of the working electrode only by a constant voltage between the working and the auxiliary electrode without elimination of the polarisation of the auxiliary electrode, causes shifts in the polarisation voltage at the working electrode and results in a shift in the selectivity and also in the sensitivity, since the process of the electrode in the auxiliary electrode causes the latters polarisation, which although it is kept within limits by using a depolariser, is so high that a reference electrode has to be used. This arrangement of 3 electrodes is connected to the potentiostat 11 in the known way. With the described measuring device it is possible to achieve a limit of detection of HCN in air of approx. 100 ppb. Cross-sensitivity occurs towards $H_2S$, NO and $Cl_2$ and this must, if necessary, be filtered out, for example with silver wadding.

2. Detection of phosgene in air.

The arrangement for the detection of phosgene differs from that mentioned under 1 only in the electrolytes. Glycerin is merely replaced by formamide. Formamide reacts quantitatively with phosgene under the formation of hydrocyanic acid:

$$COCl_2 + HCO-NH_2 \rightarrow CO_2 + 2\ HCl + HCN$$

The hydrocyanic acid is measured in the cell described under 1. The working electrode is polarized to −600 mV. The chemical reaction is specific for phosgene, so that the total arrangement is essentially only cross-sensitive to hydrocyanic acid and hydrogen sulphide, which, if necessary, have to be removed by filtering. The limit of detection of $COCl_2$ is a few ppb.

3. Detection of hydrogen sulphide in carbon monoxide.

A silver electrode coated in silver iodide or preferably silver sulphide is used as the working electrode 4 in the arrangement already described and polarized to +140 mV. The reference electrode 7 is also a silver/silver iodide or a silver/silver sulphide electrode respectively, and silver is used as the auxiliary electrode 3. The electrolyte 5 can have the same composition as that named in Example 1, but a purely organic electrolyte has also proven to be appropriate. A mixture, consisting of 10–20% polyvinyl chloride, 20–30% propylene carbonate, 50–70% diethylphthalate and approx. 1% potassium hexafluorophosphate is dissolved while hot and is filled in the electrode space. The electrolyte gels on cooling. The same electrolyte is introduced near the auxiliary electrode, however 5% lead dioxide is added as depolariser. The reaction mechanism of this polarographic cell has already been described on page 3.

This cell is particularly long-lasting and is distinguished by a high overcharge capacity 0.1 ppm of $H_2S$ are detectable.

What we claim is:

1. An electrochemical cell for the detection of a gas in a gas mixture, comprising a working electrode consisting of an ion-selective electrode, a reference electrode, an auxiliary electrode, an electrolyte, a potentiostat which is adjustable to the characteristic voltage for the component to be measured for monitoring the potential at zero current of the working electrode with respect to the reference electrode and for effecting a current flow between the auxiliary and working electrodes for polarizing the working electrode anodically or cathodically, a current measuring instrument for measuring the current between the working and auxiliary electrodes which is proportional to the concentration of the component and means for conducting the gas to the boundary between the working electrode and the electrolyte.

2. A cell as claimed in claim 1 in which the reference electrode consists of an ion-selective electrode identical to the working electrode.

3. A cell as claimed in claim 1 for the detection of hydrocyanic acid, in which the working electrode is a silver/silver iodide electrode.

4. A cell as claimed in claim 1 for the detection of phosgene, in which the electrolyte contains formamide.

5. A cell as claimed in claim 1 for the detection of hydrogen sulphide, in which the working electrode and reference electrode are one of silver/silver iodide or silver/silver sulphide electrodes; the auxiliary electrode is made of silver and the electrolyte is an alkaline organic electrolyte.

6. A cell as claimed in claim 3, 4, or 5 wherein the auxiliary electrode consists of material sufficient to render the primary reaction product of the working electrode electrolytically inactive by deposition as a result of the action of the potentiostat and the use of the material for the auxiliary electrode when the component to be measured is present in the gas under investigation.

7. A cell as claimed in claim 6, further comprising means separating the electrolyte around the reference electrode from the electrolyte between the working electrode and the auxiliary electrode and wherein the electrolyte between the working and auxiliary electrodes is thickened with respect to that around the reference electrode.

8. A cell as claimed in claim 1, in which a porous diaphragm is provided between the working electrode and the reference electrode.

9. A cell as claimed in claim 1, in which the conducting means comprises a gas chamber around the working electrode and wherein the working electrode is separated from the gas chamber by a polyethylene membrane.

10. A method for the detection of a gas in a gas mixture which comprises providing an ion-selective electrode, an auxiliary electrode, a reference electrode and an electrolyte between the electrodes; adjusting a potentiostat to the characteristic voltage for the component to be measured and connecting same to the electrodes for monitoring the potential at zero current of the working electrode with respect to the reference electrode and for effecting a current flow between the auxiliary and working electrodes to polarize the working electrode anodically or cathodically; conducting the gas to the boundary between the working electrode and the electrolyte; and measuring the current between the working and auxiliary electrodes which is proportional to the concentration of the component.

* * * * *